United States Patent
Lee

(10) Patent No.: US 6,482,443 B1
(45) Date of Patent: Nov. 19, 2002

(54) ANTLER HERB MEDICINE FERMENTED WITH CHICKEN GIZZARD AND A METHOD FOR PREPARATION THEREOF

(76) Inventor: Youn-Soo Lee, 4 March Place, Belfast Christchurch (NZ)

( * ) Notice: Subject to any disclaimer, the term of this patent is extended or adjusted under 35 U.S.C. 154(b) by 0 days.

(21) Appl. No.: 09/787,845

(22) PCT Filed: Sep. 22, 1999

(86) PCT No.: PCT/IB99/01641

§ 371 (c)(1),
(2), (4) Date: Jun. 18, 2001

(87) PCT Pub. No.: WO00/16787

PCT Pub. Date: Mar. 30, 2000

(30) Foreign Application Priority Data

Sep. 23, 1998 (KR) .......................................... 98-39441

(51) Int. Cl.⁷ .............................................. A61K 35/24
(52) U.S. Cl. ...................... 424/543; 424/550; 424/551
(58) Field of Search ............................... 424/543, 550, 424/551

(56) References Cited

U.S. PATENT DOCUMENTS 6,099,867 A    8/2000  Sim ........................... 424/549

FOREIGN PATENT DOCUMENTS

| CN | 1129589 | * | 8/1996 |
| RU | 2070048 |   | 12/1996 |
| RU | 2099067 |   | 12/1997 |
| SU | 1819606 |   | 5/1990 |

OTHER PUBLICATIONS

Kim et al., Yakhak Hoeji 38(6): 795–799 (1994). Absract.*
Patent Abstracts of Japan, Kadota Akimi, "Nutrient and Tonic Drug Prepared From Antler of Reindeer", May 17, 1988.
Abstracts, Jiqing Wang, "Taditional Chinese medicinal prepn. containing ginseng and pilose antler", Apr. 27, 1994.

* cited by examiner

Primary Examiner—Jean C. Witz

(57) ABSTRACT

Disclosed are an antler herb medicine and a preparing method thereof. The antler herb medicine is prepared by fermenting a mixture of antler and gizzard membrane at 20–60° C. In the mixture, the weight ratio of antler to gizzard membrane is within the range of 1:10 to 10:1. The antler herb medicine contains all of the efficacious components of antler, rather than selected components. Also, the fermentation of antler brings about a great change in the composition of antler, converting high molecular weight proteins into low molecular weight proteins and polypeptides, so that the antler herb medicine is greatly improved in uptake rate in the body. Thus, the antler herb medicine can show medicinal effects of antler at a small amount.

20 Claims, 3 Drawing Sheets

ANTLER HERB MEDICINE FERMENTED WITH CHICKEN GIZZARD AND A METHOD FOR PREPARATION THEREOF

TECHNICAL FIELD

The present invention relates to an antler herb medicine fermented with a chicken gizzard membrane, which is high in uptake rate in the body. Also, the present invention is concerned with a method for preparing such an antler medicine.

PRIOR ART

Antler (in Latin, Cervi parvum cornu) is defined as "the branched deciduous horn of any animal of the deer family" (Webster International Dictionary). The term 'antler' comes from the Latin 'anteoculae', meaning "in front of the eyes". Antlers are appendages of the skull, composed of a solid bony core and supported on skin covered pedicles (protuberance of the frontal bone) which are permanent tissues. While the antler is growing or regenerating, it is covered by a skin with a dense covering of fine hair that leads to the term "velvet antler" which can be applied to the growing tissue. After growth is finished, the velvet peels off to be known as "hard antler".

The formation of primary antlers is initiated after pedicle development from the periosteum of the frontal bone. Antler growth occurs at the tip containing reserve mesenchyme which can be proliferated and differentiated into chondroblasts and chondrocytes responsible for the formation of cartilage, followed by maturation, hypertrophy and calcification. The growth of antler for approximately 4 months is suspended with the increase of massive mineralization of the bone, followed by shedding the velvet skin. The hard antlers are retained during rutting season and the winter period until the time of casting. Mature antlers are composed of dead bone, comprising a thick outer layer of compact bone surrounding a central core of cancellous bone. Antler growth is depending on the photoperiod of the season. For example, wapiti grow antlers in spring and they harden in autumn. Retaining hard antlers through winter, hard antlers are cast in spring. These antlers are called "cast antlers".

In Oriental classification, animals for the traditional use of antlers are limited only to sika deer (Cervus nippon), red deer (Cervus elaphus), and Elk (Cervus canadensis).

Velvet antler has been used for thousands of years in the Orient as one of the best hematic and tonic agents in herbal medicine. Clinical observations from the Eastern world convincingly show that deer antler contains active components which influence body metabolism, protect and restore damaged organ tissue, promote immune and phagocyte functions (anti-inflammation, anti-arthritis, anti-stress), and slow the aging process. For example, according to an ancient medical document of Korea, antlers are disclosed to have energy restoration, a blood nourishing action, pain alleviation, hemopoiesis, growth promotion, heart failure remediation, and hyperfunction. In addition, it has been known to be efficacious in relieving fatigue, strengthening vitality, and promoting urination.

At present, such pharmacological efficacies of antler are now being verified. Recent animal tests and clinical tests also have shown that velvet antlers have effects of growth and development promotion in young children, senescence inhibition, erythropoiesis, heart function improvement, restoration from muscular fatigue, and pain alleviation. Particularly, velvet antlers are reported to show extensive immunological activities, including reduction of the side effects of anti-cancer agents, such as MMC and CDDP, immunopotentiation, and stress resistance.

Many attempts have been made to uncover the curious chemical make-up of antler. As a result, it is found to contain various vitals: aqueous components, such as amino acids, polypeptides, mucoproteins, and mucopolysaccharides; lipids, such as phospholipids, fatty acids, neutral fats, glycerolipids, and gangliosides; and minerals, such as calcium, magnesium, phosphorous, sodium, potassium, etc. Many of the proteins in antlers are collagen which compose cartilage tissues. Examples of the mucopolysaccharides found in antlers include hyaluronic acids and chondroitin sulfate A.

Traditional dosage forms of antlers are exemplified by decoctions and powders. Their modern forms comprise granules, tablets, pills, capsules, etc. For decoctions, antlers are boiled down alone or in combination with other herb medicines. Antler powders are prepared by drying and grinding antlers. Pharmaceutically effective components of antlers may be extracted by alcohol.

References directed to a method of preparing antler medicines can be found in many patents.

Korean Pat. Publication No. 92-1557 discloses a preparation method of antler powders, in which horns cut from sika deers are frozen at $-70°$ C., allowed to undergo stepwise refrigeration, dried in a freeze-drier, and pulverized. Korean Pat. Publication No. 94-2011 discloses an antler extract solution in 5% or less alcohol, which is prepared in such a manner that thinly cut antler pieces are immersed in diluted alcohol and the solution is concentrated under a reduced pressure, followed by inclusion of effective ingredients with cyclodextrin. In Korean Pat. Publication No. 95-10775, there is described a method for preparing an antler extract, in which antler pieces are heated at a particular temperature under pressure, subjected to sonication, filtered, and concentrated to give extracts rich in hypoxantines and gangliosides.

The pills or powders which are prepared from antlers as they are, suffer from a significant disadvantage of being low in uptake rate into the body. That is, even though they are administered, their efficacious components are not taken in the body, but excreted from the body. Extraction methods of antlers are focused on the extraction of particular components, so that all of the various components of antler are difficult to extract equally. Accordingly, the extraction methods are not recommended in traditional herb medical science because the characteristic pharmaceutical efficacy of antler, which is achieved by the interaction of entire components in balance and harmony, cannot be obtained.

Hard antlers before casting, which results from the peeling off of the velvet skin of deers, are not well used as herb medicine preparations partially because they are insufficient in efficacious components, but largely because hard antlers, made osteoid, are very low in uptake rate. Accordingly, a method of improving the uptake of hard antlers in the body allows them to be converted into a useful herb medicine.

DISCLOSURE OF THE INVENTION

Figure 1:
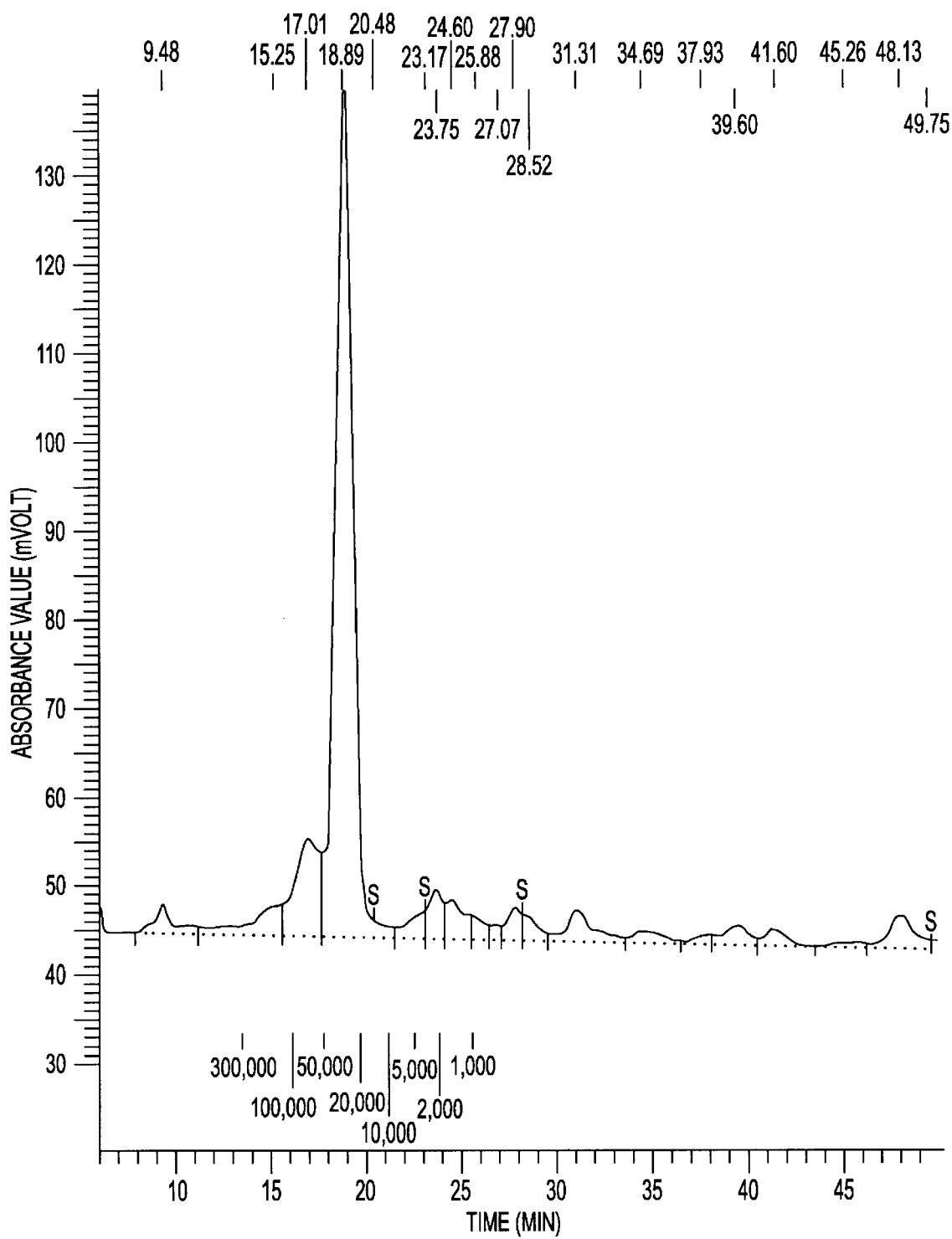
FIG. 1 is a chromatogram showing protein analysis data obtained from an antler powder (Sample A).

Leading to the present invention, the intensive and through research on antler herb medicine, repeated by the present inventors aiming to improve the uptake rate of antler in the body, resulted in the finding that the gizzard membrane of chicken ferments antlers and the fermented result is very well absorbed in vivo.

Therefore, it is an object of the present invention to overcome the above problems encountered in prior arts and to provide an antler herb medicine which retains the whole of efficacious components of antler in addition to being high in uptake efficiency in the body.

It is another object of the present invention to provide a method for preparing an antler herb medicine, which utilizes antler in its entirety at high uptake efficiency in the body.

It is another object of the present invention to provide a method for preparing an antler herb medicine, which greatly improves the uptake rate of hard antlers in the body.

Based on the present invention, the above objects could be accomplished by fermentation of antlers or hard antlers together with the gizzard membrane of chicken.

The term "antler(s)" as used herein is used to comprise velvet antler(s) and hard antler(s) both.

Best Modes For Carrying out the Preferred Embodiments

The gizzard membrane (in Latin, Endithelium Cornium Gigeraiae Galli) of chicken (Gallus domesticus Brisson), gold or yellowish brown in color, contains proteins, such as ventriculin, cystine, arginine, tryptophane and is known to show stomachic activity, nutritive and corroborant activity, and astriction (see, Korean Pharmacopoeia; Herb Medicine Standards a Commentary $3^{rd}$., Korean Medical Index Pub. May 10, 1989).

In the present invention, velvet antlers (or hard antlers) are mixed with gizzard membranes of chicken and subjected to natural fermentation. The fermentation is believed to be attributed to the bacterial flora present in the gizzard membranes. For use, the gizzard membrane is dried, ground and powered. Alternatively, the gizzard membrane is separately fermented before being mixed with velvet antlers (or hard antlers). If antlers and gizzard membranes both are in a dry state, a mixture of antlers and gizzard membranes is added with water for fermentation.

Antlers and gizzard membranes are preferably mixed at a weight ratio of antler:gizzard membrane of 10:1–1:10, more preferably 4:1–1:4, and most preferably 1:1. For example, when too little gizzard membranes are used, low fermentation effect occurs. On the other hand, when antlers are used at too low amounts, the resulting herb medicine preparation does not sufficiently show the medicinal effects of antlers. Depending on the uses of the antler products, weight ratios may be modulated within the range. In the case that the gizzard membranes are fermented in advance, a small amount of the fermented gizzard membrane suffices to ferment antlers because of enrichment of fermentative microorganisms.

The fermentation of gizzard membranes alone is preferably conducted at a temperature of 40–45° C. in consideration of the body temperature of chicken (42° C.). For the fermentation of antlers with the aid of gizzard membranes, preferable fermentation temperatures are within a range of 20–60° C. For example, a temperature lower than 20° C. lowers the fermentation efficiency. On the other hand, when the fermentation is conducted at a temperature higher than 60° C., the fermentative microorganisms die. In recognition of the body temperature of chicken, more preferable fermentation temperatures range from 40 to 45° C. It was found that, when antlers were fermented, along with the gizzard membrane, in this temperature range, the resulting antler herb medicine preparation was made suitable for the components of antler to be absorbed in the body.

As for a period of the fermentation, it depends on the weight ratio of antler and gizzard membrane, the fermentation temperature and the fermented extent of the gizzard membrane and preferably ranges from 24 to 72 hours and more preferably from 48 to 72 hours.

In order to remove harmful bacteria or other microorganisms, the fermented solution may be sterilized in an ordinary process, for example, by heat or chemicals.

After being sterilized, the fermented antler solution may be formulated into forms to be convenient for eating. For example, the fermented solution may be dried and milled to produce powders. In addition, the powders may be formed into tablets, capsules, and soft capsules. Further, the fermented solution may be aliquoted into dosages.

A better understanding of the present invention may be obtained in light of the following examples which are set forth to illustrate, but are not to be construed to limit the present invention.

Example I

Preparation of Antler Herb Medicine

Gizzard membranes of chicken were washed cleanly, dried and milled. Separately, clean antlers were dried and pulverized. These materials were mixed at an equal amount and added with water, followed by fermentation at 42° C. for 60° C. After completion of the fermentation, the fermented solution was thermally treated at 134° C. for 30 min or longer, dried and finely pulverized to produce a powder of an antler herb medicine.

Comparative Example I

The same antler as that used in Example I (that is, some of the antlers obtained from a deer was used in Example I and some was used in Comparative Example I) was dried after being cleaned, and powdered as finely as in Example I.

Comparative Example II

The same gizzard membrane as that used in Example I was dried cleanly, dried and powdered as finely as in Example I.

Example II

Composition Change in Antler Herb Medicine After and Before Fermentation

An measurement was made of the compositions of the antler herb medicine obtained in Example I, the powdered antler obtained in Comparative Example I, and the powdered gizzard membrane obtained in-Comparative Example II.

Samples
  Sample A: Antler powder of Comparative Example I
  Sample B: Gizzard membrane powder of Comparative Example
  Sample C: Antler herb medicine of Example I before being sterilized.
Moisture Content in the Samples (dried at 105° C.)
  Sample A: 4.1%
  Sample B: 8.2%
  Sample C: 4.7%
Total Lipids
  Sample A: 2.0% of dried matter
  Sample B: 0.9% of dried matter
  Sample C: 1.4% of dried matter
Ash Content (Combusted at 550° C.)
  Sample A: 44.3% of dried matter
  Sample B: 1.5% of dried matter
  Sample C: 24.3% of dried matter Mineral Quantification The dried matters of the samples were analyzed for mineral content and the results are given in Table 1, below.

TABLE 1

| Samples | N (%) | P (%) | S (%) | Mg (%) | Ca (%) | Na (%) | K (%) | Mn (ppm) | Zn (ppm) | Cu (ppm) | Fe (ppm) | Co (ppm) | Se (ppm) |
|---|---|---|---|---|---|---|---|---|---|---|---|---|---|
| A | 7.84 | 5.60 | 0.30 | 0.35 | 13.94 | 0.42 | 0.22 | 22 | 68 | 5 | 405 | 0.15 | 0.15 |
| B | 13.08 | 0.29 | 0.97 | 0.03 | 0.12 | 0.03 | 0.15 | 10 | 20 | 73 | 127 | 0.09 | 0.51 |
| C | 10.76 | 3.46 | 0.66 | 0.17 | 7.74 | 0.18 | 0.13 | 12 | 46 | 39 | 249 | 0.41 | 0.38 |

Microorganism Analysis

Sample A: it was incubated aerobically and anaerobically in non-selective media and an examination was made of the number and type of the microbes grown. As measured at 30° C., aerobes were found to amount, in total, to $4.3 \times 10^3$ c.f u. per gram. Total coliform showed 23 M.P.N. per gram while Bacillus cereus was grown to a quantity of $2.7 \times 10^3$ c.f.u. per gram. No yeasts and moulds were detected.

Sample B: after being incubated in non-selective media in the presence and the absence of oxygen, microbes were grown as shown in Table 2, below.

TABLE 2

| Microbes Detected | Quantity |
|---|---|
| Total Aerobes (measured at 30° C.) | $4.4 \times 10^4$ (c.f.u. per gram) |
| Total Coliform | 170 (M.P.N. per gram) |
| Bacillus cereus | $2.7 \times 10^3$ (c.f.u. per gram) |
| Yeast and Mould | $5.5 \times 10^2$ (c.f.u. per gram) |

As apparent from Table 2, a large quantity of various microbes were contained in the gizzard membrane.

Sample C: it was incubated aerobically and anaerobically in non-selective media. Then, the microbes grown were incubated in selective media for coagulase-positive Staphylococci, Lactobacilli, yeasts and moulds, and *Bacillus cereus*. As a result, *Enterococcus faecium, Enterococcus faeclis, Bacillus cereus*, and *Bacillus brevis* were detected.

This analysis showed that many microbes, such as bacteria, yeasts and moulds, much of which were provided from gizzard membrane, were involved in the fermentation of a mixture of antler and gizzard membrane.

Protein Analysis

The samples A, B and C were analyzed for their protein contents. In this regard, HPLC (High Performance Liquid Chromatography) was utilized. The components thus separated were measured for absorbance at 280 nm, to quantify the peptides and proteins contained in the samples. Aromatic amino acids, such as tyrosine and tryptophane, of proteins absorb the light of 280 nm in proportion to their concentration. In contrast, carbohydrates and lipids cannot absorb the light at the wavelength, so that they are not detected.

Before analysis, proteins and peptides were extracted from the samples. To this end, each of the samples was placed, together with an analyzing buffer, in an ultrasonication bath. sonication allowed efficacious components to be extracted into the buffer. The extracts were filtered and washed and the filtrates were loaded on chromatography column.

As a rule, the period of time which it takes for each component to be eluted from the column is dependent on the size of each component. That is, larger sizes come from earlier, and smaller sizes later. Therefore, pure proteins whose molecular weights are known can be used to determine the molecular weights of sample compounds. Because the separation of sample compounds is accomplished on the basis of their sizes rather than their molecular weights, the obtained molecular weights are approximate values. With very useful information, the approximate values obtained, however, are accurate enough to be applicable for general uses.

Figure 2:
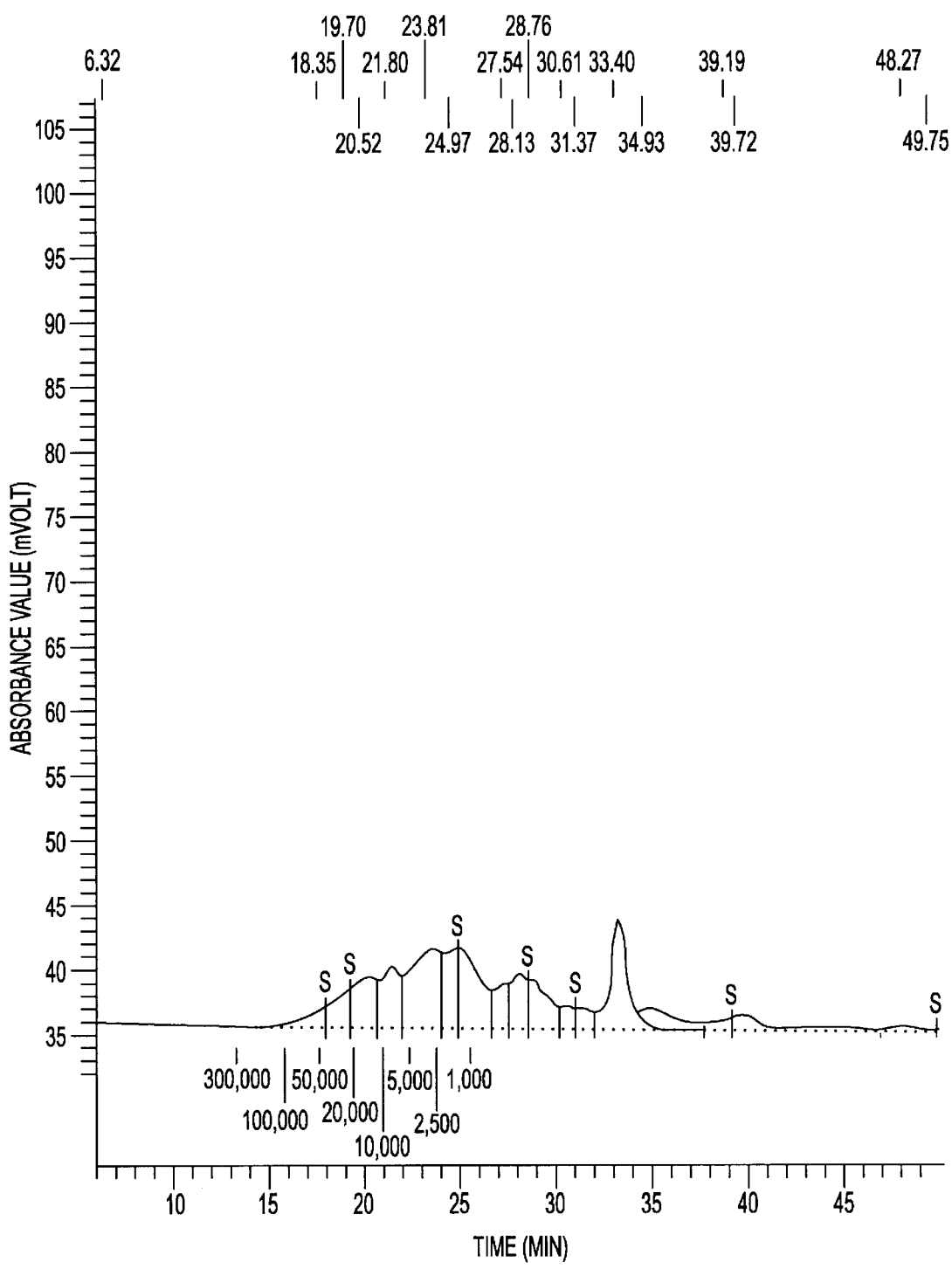
FIG. 2 is a chromatogram showing protein analysis data obtained from a gizzard membrane (Sample B).
Figure 3:
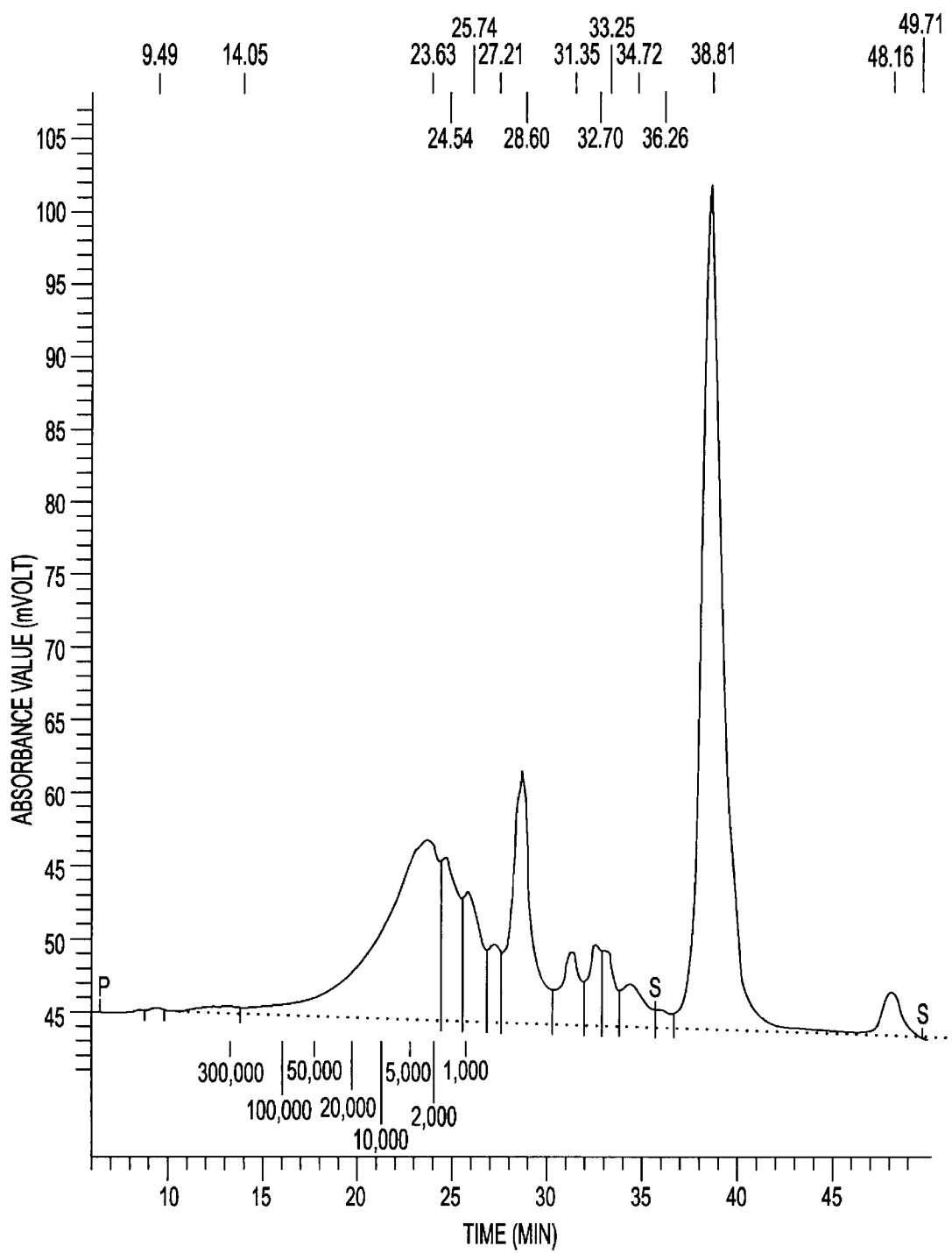
FIG. 3 is a chromatogram showing protein analysis data obtained from an antler herb medicine according to the present invention (Sample C).

The protein analysis data obtained from the sample A, B and C are shown in FIGS. 1, 2 and 3, respectively. In the chromatograms of FIGS. 1 to 3, each peak represents the elution of the proteins of similar sizes at the time indicated on the X axis. Since absorbance values at 280 nm are, in scale, marked on the Y axis and the molecular weight of proteins is in inverse proportion to the period of time, the peaks give the information regarding the molecular weights of the proteins contained in the samples.

An measurement was made of the peak time, the peak areas and the proportions of individual peak areas to the total peak area in the chromatograms, and the results are summarized in Tables 3 to 5, below.

TABLE 3

Analysis of Proteins Contained in Sample A

| Peak No. | Time (min) | Peak Area | % Peak | Mw. Range | Log. Mw | Putative Mw. |
|---|---|---|---|---|---|---|
| 1 | 9.5 | 217878 | 2.3 | J:≧300,000 | 6.12 | 1326250 |
| 2 | 15.2 | 420104 | 4.4 | I:100,000–300,000 | 5.19 | 153200 |
| 3 | 17.0 | 1006054 | 10.5 | H:50,000–100,000 | 4.86 | 72500 |
| 4 | 18.9 | 5679980 | 59.1 | G:25,000–50,000 | 4.49 | 31050 |
| 5 | 20.5 | 4654 | 0.1 | F:10,000–25,000 | 4.16 | 14550 |
| 6 | 23.2 | 191062 | 2.0 | D:2,500–5,000 | 3.58 | 3750 |
| 7 | 23.8 | 280509 | 2.9 | D:2,500–5,000 | 3.44 | 2750 |
| 8 | 24.6 | 580966 | 2.9 | C:1,000–2,500 | 3.25 | 1750 |
| 9 | 25.9 | 109563 | 1.1 | B:500–1,000 | 2.94 | 850 |
| 10 | 27.1 | 60234 | 0.6 | A:≦500 | 2.65 | 450 |
| 11 | 27.9 | 190846 | 2.0 | A:≦500 | 2.44 | 250 |
| 12 | 28.5 | 155036 | 1.6 | A:≦500 | 2.28 | 200 |
| 13 | 31.3 | 334384 | 3.5 | A:≦500 | 1.53 | 50 |
| 14 | 34.7 | 131609 | 1.4 | A:≦500 | 0.57 | 0 |
| 15 | 37.9 | 48967 | 0.5 | A:≦500 | −0.42 | 0 |
| 16 | 39.6 | 140320 | 1.5 | A:≦500 | −0.95 | 0 |
| 17 | 41.6 | 108916 | 1.1 | A:≦500 | −1.62 | 0 |
| 18 | 45.3 | 30842 | 0.3 | A:≦500 | −2.89 | 0 |
| 19 | 48.1 | 210160 | 2.2 | A:≦500 | −3.94 | 0 |
| 20 | 49.7 | 2014 | 0.0 | A:≦500 | −4.56 | 0 |

TABLE 4

Analysis of Proteins Contained in Sample B

| Peak No. | Time (min) | Peak Area | % Peak | Mw. Range | Log. Mw | Putative Mw. |
|---|---|---|---|---|---|---|
| 1 | 6.3 | 4415 | 0.1 | J:≧300,000 | 6.55 | 3564450 |
| 2 | 18.4 | 151471 | 3.7 | G:25,000–50,000 | 4.60 | 39750 |
| 3 | 19.7 | 193807 | 4.7 | F:10,000–25,000 | 4.33 | 21200 |
| 4 | 20.5 | 286387 | 6.9 | F:10,000–25,000 | 4.16 | 14300 |
| 5 | 21.8 | 318766 | 7.7 | F:5,000–10,000 | 3.88 | 7600 |
| 6 | 23.8 | 621606 | 15.0 | D:2,500–5,000 | 3.43 | 2700 |
| 7 | 25.0 | 297958 | 7.2 | C:1,000–2,500 | 3.16 | 1450 |
| 8 | 25.2 | 435921 | 10.5 | C:1,000–2,500 | 3.10 | 1250 |

TABLE 4-continued

Analysis of Proteins Contained in Sample B

| Peak No. | Time (min) | Peak Area | % Peak | Mw. Range | Log. Mw | Putative Mw. |
|---|---|---|---|---|---|---|
| 9 | 27.5 | 175198 | 4.2 | A:≤500 | 2.53 | 350 |
| 10 | 28.1 | 222388 | 5.4 | A:≤500 | 2.38 | 250 |
| 11 | 28.8 | 278490 | 6.7 | A:≤500 | 2.22 | 150 |
| 12 | 30.6 | 87844 | 2.1 | A:≤500 | 1.72 | 50 |
| 13 | 31.4 | 91866 | 2.2 | A:≤500 | 1.52 | 50 |
| 14 | 33.4 | 538336 | 13.0 | A:≤500 | 0.94 | 0 |
| 15 | 34.9 | 182481 | 4.4 | A:≤500 | 0.50 | 0 |
| 16 | 39.2 | 55435 | 1.3 | A:≤500 | −0.82 | 0 |
| 17 | 39.7 | 169532 | 4.1 | A:≤500 | −0.99 | 0 |
| 18 | 48.3 | 31181 | 0.8 | A:≤500 | −3.99 | 0 |
| 19 | 49.8 | 254 | 0.0 | A:≤500 | −4.56 | 0 |

TABLE 5

Analysis of Proteins Contained in Sample C

| Peak No. | Time (min) | Peak Area | % Peak | Mw. Range | Log. Mw | Putative Mw. |
|---|---|---|---|---|---|---|
| 1 | 9.5 | 9441 | 0.1 | J:≥300,000 | 6.12 | 1320050 |
| 2 | 14.0 | 79616 | 0.7 | I:100,000–300,000 | 5.40 | 249550 |
| 3 | 23.6 | 2648144 | 23.8 | D:2,500–5,000 | 3.47 | 2950 |
| 4 | 24.5 | 660963 | 5.9 | C:1,000–2,500 | 3.26 | 1800 |
| 5 | 25.7 | 567767 | 5.1 | B:500–1,000 | 2.97 | 950 |
| 6 | 27.2 | 268541 | 2.4 | A:≤500 | 2.61 | 400 |
| 7 | 28.6 | 1179895 | 10.6 | A:≤500 | 2.26 | 200 |
| 8 | 31.4 | 362177 | 3.3 | A:≤500 | 1.52 | 50 |
| 9 | 32.7 | 294764 | 2.7 | A:≤500 | 1.14 | 0 |
| 10 | 33.3 | 212498 | 1.9 | A:≤500 | 0.99 | 0 |
| 11 | 34.7 | 262701 | 2.4 | A:≤500 | 0.56 | 0 |
| 12 | 36.3 | 65728 | 0.6 | A:≤500 | 0.10 | 0 |
| 13 | 38.8 | 4317169 | 38.8 | A:≤500 | −0.70 | 0 |
| 14 | 48.2 | 208956 | 1.9 | A:≤500 | −3.95 | 0 |
| 15 | 49.7 | 1001 | 0.0 | A:≤500 | −4.54 | 0 |

TABLE 6

Comparison of Proteins Contained in Samples A, B and C

| Mw Range | % Area A | % Area B | % Area C | Total Area A | Total Area B | Total Area C |
|---|---|---|---|---|---|---|
| A:≤500 | 14.7 | 44.2 | 64.4 | 1413327 | 1833004 | 7173430 |
| B:500–1,000 | 1.1 | | 5.1 | 109563 | | 567767 |
| C:1,000–2,500 | 2.9 | 32.7 | 5.9 | 280966 | 1355485 | 660963 |
| D:2,500–5,000 | 4.9 | | 23.8 | 471571 | | 2648144 |
| E:5,000–10,000 | | 7.7 | | | 318766 | |
| F:10,000–25,000 | 0.1 | 11.8 | | 4654 | 480194 | |
| G:25,000–50,000 | 59.1 | 3.7 | | 5679980 | 151471 | |
| H:50,000–100,000 | 10.5 | | | 1006054 | | |
| J:100,000–300,000 | 4.4 | | 0.7 | 420104 | | 79616 |
| J:≥300,000 | 2.3 | 0.1 | 0.1 | 217878 | 4415 | 9441 |
| Total | 100.0 | 100.0 | 100.0 | 9604097 | 4143336 | 11139361 |

As apparent from the data of Table 6, there is a large difference in composition between the antler herb medicine fermented according to the present invention and the antler which was not fermented. Particularly, the antler herb medicine of the present invention is even richer in low molecular weight proteins and polypeptides than is the antler which is not fermented, as shown in FIG. 3 and Table 6.

INDUSTRIAL APPLICABILITY

Taken together, the data obtained in the above examples demonstrate that the fermentation of antler brings about a great change in the composition of antler, converting high molecular weight proteins into low molecular weight proteins and polypeptides. As a rule, because low molecular weight proteins or peptides are absorbed faster than high molecular weight proteins, the antler herb medicine which is fermented with gizzard membranes, according to the present invention, is far superior to conventional antler herb medicines in uptake rate in the body. Therefore, the antler herb medicine of the present invention shows the medicinal effects of antler at a smaller amount than do conventional antler herb medicines.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method of preparing an antler herb medicine, in which an antler is mixed with a gizzard membrane of a chicken and subjected to a fermentation, the method comprising:

preparing the gizzard membrane including cleaning, drying and milling the gizzard membrane of the chicken;

preparing the antler including drying and pulverizing the dried antler;

obtaining a mixture having the prepared antler and the prepared gizzard membrane at an antler:gizzard membrane weight ratio of 10:1 to 1:10;

fermenting the mixture including adding water to the mixture and heating the mixture in the water at a temperature 20–60° C. for 24–72 hours, wherein the gizzard membrane is used as a fermenting enzyme;

obtaining a sterilized mixture of the fermented mixture; and preparing a pharmaceutical form of the sterilized mixture including drying and pulverizing the sterilized mixture.

2. The method as set forth in claim 1, wherein the mixture has the antler:gizzard membrane weight ratio of 4:1 to 1:4.

3. The method as set forth in claim 1, wherein the mixture has the antler:gizzard membrane weight ratio of 1:1.

4. A method of preparing an antler herb medicine, in which an antler is mixed with a gizzard membrane of a chicken, the method comprising:

preparing a fermented gizzard membrane of the chicken including fermenting the gizzard membrane at a temperature 40–45° C. for 24–72 hours;

preparing the antler including drying and pulverizing the dried antler;

preparing a mixture including mixing the prepared antler and the fermented gizzard membrane at an antler:fermented gizzard membrane weight ratio of 10:1 to 1:10, wherein the fermented gizzard membrane is used as a fermenting enzyme;

obtaining a sterilized mixture of the prepared mixture; and preparing a powder form of the sterilized mixture including drying and pulverizing the sterilized mixture.

5. An antler herb medicine, prepared by the method of claim 1.

6. The antler herb medicine as set forth in claim 5, further comprising at least one herb drug material which is compatible with the antler.

7. The antler herb medicine as set forth in claim 5, which is in a dosage form of powders, granules, tablets, capsules, soft capsules, or decoctions.

8. The antler herb medicine as set forth in claim 5, further comprising at least one pharmaceutically acceptable and pharmacologically inactive formulating agent.

9. The method as set forth in claim 1, wherein the antler is a velvet antler or a hard antler.

10. The antler herb medicine as set forth in claim 6, further comprising at least one pharmaceutically acceptable and pharmacologically inactive formulating agent.

11. The method as set forth in claim 4, wherein the antler is a velvet antler or a hard antler.

12. The method as set forth in claim 1, wherein the obtaining of the sterilized mixture comprises thermally treating the fermented mixture at a temperature of about 134° C for 30 minutes or more.

13. The method as set forth in claim 4, wherein the preparing of the mixture further includes fermenting the mixed prepared antler and fermented gizzard membrane at a temperature of 20–60° C. for 24–72 hours.

14. The method as set forth in claim 4, wherein the obtaining of the sterilized mixture comprises thermally treating the prepared mixture at a temperature of about 134° C for 30 minutes or more.

15. The method as set forth in claim 4, wherein the mixed mixture has the antler:fermented gizzard membrane weight ratio of 4:1 to 1:4.

16. The method as set forth in claim 4, wherein the mixed mixture has the antler:fermented gizzard membrane weight ratio of 1:1.

17. An antler herb medicine, prepared by the method of claim 4.

18. The antler herb medicine as set forth in claim 17, further comprising at least one herb drug material which is compatible with the antler.

19. The antler herb medicine as set forth in claim 17, which is in a dosage form of powders, granules, tablets, capsules, soft capsules, or decoctions.

20. The antler herb medicine as set forth in claim 17, further comprising at least one pharmaceutically acceptable and pharmacologically inactive formulating agent.

* * * * *